United States Patent [19]

Raab

[11] Patent Number: 5,175,380
[45] Date of Patent: Dec. 29, 1992

[54] PROCESS FOR REMOVING IMPURITIES FROM PERFLUORINATED ALKYL BROMIDES OR ALKYLENE DIBROMIDES

[75] Inventor: Klaus Raab, Burgkirchen, Fed. Rep. of Germany

[73] Assignee: Hoechst Aktiengesellschaft, Frankfurt am Main, Fed. Rep. of Germany

[21] Appl. No.: 882,843

[22] Filed: May 14, 1992

[30] Foreign Application Priority Data

May 17, 1991 [DE] Fed. Rep. of Germany ....... 4116121

[51] Int. Cl.$^5$ ............... C07C 17/20; C07C 17/38; C07C 19/08
[52] U.S. Cl. ................... 570/177; 570/178; 570/179; 570/180
[58] Field of Search ............ 570/177, 178, 179, 180

[56] References Cited

U.S. PATENT DOCUMENTS

| | | | |
|---|---|---|---|
| 4,801,763 | 1/1989 | Maul et al. ............... | 570/177 |
| 5,051,535 | 9/1991 | von Werner . | |
| 5,073,651 | 12/1991 | Raab . | |
| 5,113,026 | 5/1992 | Raab . | |

FOREIGN PATENT DOCUMENTS

0194781 9/1986 European Pat. Off. .
4116361 1/1992 Fed. Rep. of Germany .

OTHER PUBLICATIONS

Haszeldine, R. N., *J. Chem. Soc.*: pp. 3761–3768 (1953).
Huang, B., et al., *Chem. Abs.* 102:78304, No. 78312x (1985).

*Primary Examiner*—Alan Siegel

[57] ABSTRACT

Mixtures of perfluorinated alkyl bromides or alkylene dibromides containing perfluorinated iodine compounds are irradiated with electromagnetic radiation in the wavelength range from 230 to 500 nm and brought into contact, either during the irradiation or directly thereafter, with at least one of the following agents: active charcoal, certain finely divided metals, lower aliphatic alcohols, chlorine, bromine, oxygen, hydrogen peroxide, aqueous or alcoholic solutions of alkali metal compounds with certain inorganic anions or lower aliphatic alcohols. After removal of the agent and if appropriate distillation, products which contain less than 0.0005% by weight of iodine compounds and can be employed, for example, in the medical sector can be obtained.

9 Claims, No Drawings

PROCESS FOR REMOVING IMPURITIES FROM PERFLUORINATED ALKYL BROMIDES OR ALKYLENE DIBROMIDES

The invention relates to a process for the purification of impure perfluorinated alkyl bromides or alkylene dibromides which essentially contain, as impurities, small amounts of perfluorinated alkyl iodides or alkylene diiodides, called "iodoalkane compounds" below.

Perfluorinated alkyl-bromine compounds, for example perfluorohexyl bromide or perfluorooctyl bromide, are employed, inter alia, for medical purposes, where they are administered (introduced into the body of the patient), for example, intravenously or gastrointestinally. They are used, for example, as contrast media for examinations with X-rays or with ultrasound, for detecting tumors, for organ perfusion and in aqueous emulsion as a blood substitute. Exceptionally high purity requirements are imposed for these fields of use, so that undesirable physiological actions of impurities are to be largely restricted or avoided completely.

Perfluorinated alkyl-bromine compounds such as are used, for example, for the abovementioned purposes can be prepared in various ways, but these as a rule give products which do not comply with the medical purity requirements and either cannot be employed for these fields of use or have to be purified in an expensive manner with high losses.

Reaction of the corresponding perfluorinated iodoalkane compounds with elemental bromine or bromides is a possible preparation process for perfluorinated alkyl bromides or alkylene dibromides, but this leads to products which still contain starting compounds which often can be removed only with difficulty because the boiling points lie close to one another.

Haszeldine, J. Chem. Soc., 1953, pages 3,766 and 3,767 describes the reaction of perfluoroalkyl iodides with a 10% excess of bromine under irradiation with ultraviolet light for 7 days. $C_3$- and $C_4$-Perfluoroalkyl bromides are obtained in this way in a yield of 95 to 98%, and $C_5$-$C_6$-perfluoroalkyl bromides in a yield of 90 to 91%. No information is given on the nature of the UV radiation or any further purification.

Huang Bingnan and Huang Weiyuan, Shanghai Inst. Org. Chem. Acad. Sinica, Huaxue Xuebao, 1984, 42 (10), pages 1,106 to 1,108 (C.A. 102, 78312x) report analogously on the bromination of perfluoroalkyl-iodine compounds with bromine using UV radiation. For example, $Cl(CF_2)_4Br$ can be produced from $Cl(CF_2)_4I$ in a yield of 93% with somewhat less than the equimolar amount of bromine by irradiation for 50 hours. Data on the nature of the UV radiation are also lacking here.

EP 194,781 A1 describes a process with which, inter alia, perfluorinated alkylene dibromids can be prepared by reaction of corresponding alkylene dihalides (in which the halogen can be Cl and/or I) with excess bromine at temperatures of up to 180° C. without using UV radiation. For example, 99% of $Br(CF_2)_6Br$ and 1% of starting compound are obtained from $I(CF_2)_6Cl$ and bromine at 150° C. German Offenlegungsschrift (DE-OS) 41 16 361 proposes reaction of perfluoroalkyl iodides with elemental bromine at 100° to 290° C. without using UV radiation. Yields of perfluoroalkyl bromides of up to 97% and conversions of more than 99.9% are obtained at temperatures of 190° C. However, this process, like that described in EP 194 781 A1, has the disadvantage that high temperatures or very long reaction times have to be used for very high conversions, and these are accompanied by considerable corrosion problems and safety risks, because of the use of aggressive bromine in pressure-tight apparatuses, and promote the formation of undesirable by-products.

Preparation processes for perfluorinated alkyl-bromine compounds such as are described in DE-OS 39 37 567 (U.S. Pat. No. 5,073,651) and are proposed in DE-OS 40 04 783 (U.S. Pat. No. 5,051,535) and 40 18 913 (U.S. patent application Ser. No. 07/713,962 now U.S. Pat. No. 5,113,026 issued May. 12, 1992 have no particular corrosion problem. In these, perfluoroalkyl iodides are reacted with bromide ions, which are present as salts with certain cations, with or without the use of a dipolar aprotic solvent, it being possible to carry out the reaction in the presence of certain metal complex compounds or an alkali metal salt of a hydroxyalkanesulfinic acid in order to improve the yields of perfluoroalkyl bromide.

In all cases, the perfluorinated alkyl- or alkylene-bromine compounds produced still contain portions of the corresponding iodine compounds which are too high for the uses mentioned above, even if the content of perfluorinated alkyl- or alkylene-bromine compound has been increased considerably, for example to 99% or more, by subsequent distillation.

There was therefore the object of discovering a process which enables the small content of corresponding iodine compounds in mixtures essentially containing perfluorinated alkyl- and alkylene-bromine compounds to be decreased considerably, in order to achieve extended possible uses of the bromine compounds.

The object is achieved by a process for removing impurities from a compound or compounds of the formula

$$X(CF_2)_nBr \qquad (I)$$

in which

X is F, $(CF_3)_2CF$ or Br and n is a number from 2 to 16, which comprises irradiating the preferably liquid mixture to be purified with electromagnetic radiation in the wavelength range from 230 to 500 nm, bringing the mixture into contact, during or after the irradiation, with at least one of the following agents: active charcoal, a finely divided solid from the series comprising Cu, CuI, Ag, Mg, Zn, Al, Mn, Fe, Co, Ni and an alkali metal borohydride, chlorine, bromine, oxygen, aqueous solutions of $H_2O_2$, other inorganic peroxidic compounds or alkali metal salts with the following anions: $SO_3^{2-}$, $S_2O_3^{2-}$, $PO_3^{3-}$, $NO_2^-$, $CO_3^{2-}$, $HCO_3^-$, $BrO_3^-$, $ClO_3^-$, aqueous or alcoholic solutions of alkali metal hydroxides, iodides or alcoholates or lower aliphatic alcohols, removing the agent after the treatment has ended and, if necessary, washing the product with water and distilling it.

The mixtures to be purified according to the invention should consist to the extent of at least 95% by weight, preferably to the extent of at least 99% by weight and in particular to the extent of at least 99.5% by weight (all the percent by weight data are based on the mixture), of a compound or plurality of compounds of the formula (I). Because of its good action and the favorable usefulness of the purified mixtures, the process according to the invention is preferably used on mixtures which essentially consist of at least one compound of the formula (I) in which X is F or Br and n is a number from 4 to 10. Mixtures which essentially consist of at least one compound of the formula (I) in which X is F and n is a number from 6 to 8 are employed in particular.

The mixtures to be purified can be treated according to the invention in gaseous form, but they are advantageously treated in the liquid state.

The temperature at which the mixtures are irradiated should be 0° to 100° C., preferably 5° to 80° C., above the melting point of the mixture, but not above 200° C., since undesirable side reactions may occur at higher temperatures. In general, temperatures below 0° C. advantageously will also not be used, in order to avoid relatively expensive cooling. The temperature during the irradiation can vary within the limits mentioned. The temperature of the mixture to be treated should likewise lie within the abovementioned temperature ranges directly after the irradiation while the mixture is brought into contact with the abovementioned agents; this temperature can be the same as the temperature during the irradiation or can differ from this temperature.

The process according to the invention is carried out under normal atmospheric pressure or under the autogenous pressure of the reaction mixture.

The mixture to be purified according to the invention should contain up to 1% by weight of perfluorinated iodoalkane compounds. The novel process can in principle also be used for mixtures which contain more than 1% by weight of perfluorinated iodoalkane compounds, but then usually requires high irradiation outputs and/or long irradiation times in order to achieve a desired low content of iodine compounds, so that as a rule it is advantageous first to remove relatively large amounts of undesirable iodine compounds from the mixture by a different route, for example by distillation, and only then to use the process according to the invention. A mixture which contains not more than 0.1% by weight of perfluorinated iodoalkane compounds is preferably treated by the novel process.

The mixture to be purified is irradiated with electromagnetic radiation in the wavelength range from 230 to 500 nm. Good results are often obtained if radiation is used which lies in the wavelength range from 280 to 450 nm to the extent of at least 50% of its total intensity and in which the intensity in the wavelength range below 260 nm is less than 10% of the total intensity. If the agent with which the mixture to be purified is brought into contact is chlorine or bromine, a wavelength range of 350 to 500 nm is preferably employed for the irradiation.

Suitable radiation sources are low pressure, medium pressure or high pressure gas discharge lamps with a filling of, for example, mercury, noble gases, hydrogen or deuterium. The mercury vapor high pressure lamps with filters which absorb the electromagnetic radiation with a wavelength below about 230 nm, preferably below about 260 nm, or convert it into longer-wavelength UV light by luminescence, and the xenon high pressure lamp may be mentioned in particular. Lamps which radiate a high proportion of visible light in the short-wavelength part of the spectrum (violet and blue), such as, for example, special fluorescent lamps of the type TL/03 or TL/52 from Osram, Berlin/Munich, Federal Republic of Germany, are furthermore suitable.

Corona discharge lamps, a special form of gas discharge lamp, with a noble gas or noble gas and mercury vapor filling, can also be employed, as can a xenon-chlorine laser(wavelength 308 nm) or arc lamps. Powerful halogen lamps, which are an improved version of the tungsten wire incandescent lamps, may also be suitable.

Suitable absorbents for lamps of lower radiation capacity are special glasses, for example the glass "Heralux ®" or a borosilicate glass having a particularly low thermal expansion (®Duran 50 from Heraeus/Hanau, Federal Republic of Germany). For lamps of higher capacity, it is advisable to employ a liquid absorbent, which can simultaneously serve to cool the lamp in a cooled circuit Methanol or ethylene glycols, for example, are suitable The space in which the reaction according to the invention takes place should advantageously be adapted to suit the radiation source, so that as far as possible all the radiation reaches the reaction mixture Radiation sources which are immersed in the liquid mixture to be purified, for example, are particularly suitable for this purpose. If the external wall of the reaction vessel is transparent to radiation of the immersion lamp in the wavelength range from 270 to 500 nm, it is advisable to apply a reflecting coating or a corresponding covering, for example of aluminum foil, to the external wall.

If the agent with which the mixture to be purified is brought into contact is chosen from the group comprising oxygen, chlorine, bromine, lower aliphatic alcohols and aqueous or alcoholic solutions of the inorganic compounds mentioned, excluding the alkali metal iodides, the contact can take place during the irradiation, i.e. in the same zone in which the irradiation is carried out, it being possible to intensify the contact, for example by stirring.

In the case of agents which are opaque to radiation, such as active charcoal or finely divided metal powders, the irradiation and treatment are advantageously separate. It is advantageous here to pass the mixture to be purified through a zone in which the irradiation takes place and then through a zone in which it comes into contact with one of the agents mentioned, if necessary in circulation several times in succession. However, the contact with all the agents mentioned can also take place only after the irradiation has ended.

The suitable agents have already been described above. If solutions are used, these should as far as possible contain 0.1 g or more of the dissolved substance per 100 g of solution. Suitable lower aliphatic alcohols are those which contain 1 to 6 carbon atoms, preferably 1 to 4 carbon atoms, in the molecule. 1 to 50 g of these are advantageously used per 100 g of mixture to be purified. The amounts of oxygen, chlorine or bromine or the inorganic compounds, such as an alkali metal borohydride, inorganic peroxidic compounds, for example hydrogen peroxide, alkali metal persulfates, perborates or persilicates, and furthermore alkali metal hydroxides, sulfites, thiosulfates, phosphites, nitrites, carbonates, bicarbonates, bromates or chlorates, and also of the alkali metal alcoholates employed are at least the equivalent amounts which are needed for reaction of the iodine atoms contained in the mixture to be purified. However, an excess of the inorganic substances which is 1.5 to 10 times, preferably 2 to 5 times the amount equivalent for reaction of the iodine in the case of contents of perfluorinated iodoalkane compounds in the mixture of the order of 0.1 to 1% by weight, and 5 to 500 times, preferably 10 to 100 times the amount equivalent for reaction of the iodine in the case of contents of perfluorinated iodoalkane compounds in the mixture of up to 0.1% by weight is advantageously used.

Any desired excess of agents such as concentrated alkali metal iodide solution, active charcoal and finely divided metals, such as copper, silver, magnesium, zinc, aluminum, manganese, iron, cobalt or nickel, can be used, and 2 to 10 g of the agent per 100 g of mixture to be purified are advantageously employed.

The following agents are preferably used: an aqueous solution of an alkali metal hydroxide, carbonate, bicarbonate or thiosulfate, and furthermore active charcoal, finely divided magnesium or finely divided zinc.

In another preferred embodiment of the process according to the invention, chlorine or bromine is employed together with electromagnetic radiation in the wavelength range from 350 to 500 nm, as already mentioned above.

The irradiation of the product to be purified and the bringing into contact with the agents described are continued until the low or no longer detectable content of perfluorinated iodoalkane compounds which is desired in the mixture to be purified is determined, for example by capillary gas chromatography determination. The irradiation times can differ widely. They depend, inter alia, on the nature and amount of perfluorinated iodoalkane compounds, the nature of the agent added and the nature and intensity of the irradiation. Irradiation times of 0.2 to 20 hours are in general sufficient.

At the end of the irradiation and, if necessary, after an after-reaction time with the agent used, this is removed from the purified product, for example by filtration, decanting, if appropriate using centrifugal forces, by separation of two liquid phases in a separating funnel or by other known separating methods. If aqueous or alcoholic agents are used, washing (stirring, extraction by shaking) of the purified product with water and removal of the washing liquid now advantageously follow. If necessary, the purified product is then subjected to fractional distillation, reduced pressure advantageously being applied if the boiling point of the main fraction under normal atmospheric pressure is above 200° C.

The product purified as described contains a considerably decreased content of perfluorinated iodoalkane compounds which, depending on the starting mixture and the treatment conditions, can be below 0.0005% by weight, based on the product to be purified.

Such a product corresponds to the exceptionally high purity requirements imposed for various uses in the medical sector.

The process according to the invention does not require high temperatures and/or high pressures, which cause apparatus difficulties, especially if chemically aggressive agents are used.

The following examples are intended to illustrate the invention.

EXAMPLE 1

400 g of perfluorooctyl bromide of the formula $CF_3(CF_2)_7Br$ are introduced into a cylindrical irradiation apparatus (internal diameter: 5.5 cm, height: 20 cm) with jacket cooling, a Heraeus immersion lamp, comprising the TQ 150 mercury high pressure radiation source and an immersion tube of Duran 50 for absorption of the short-wavelength UV radiation (radiation flux of 300 to 580 nm: about 30 watt, about 50% of the total radiation intensity lies in the wavelength range from 350 to 450 nm), intensive cooler with a $CaCl_2$ drying tube, internal thermometer and magnetic stirring fish. According to capillary gas chromatography determination, the perfluorooctyl bromide contains 0.017% (w/w) of perfluorohexyl iodide of the formula $CF_3(CF_2)_5I$, 0.011% (w/w) of perfluoroheptyl iodide of the formula $CF_3(CF_2)_6I$ and 0.018% (w/w) of perfluorooctyl iodide of the formula $CF_3(CF_2)_6I$. The solution is stirred at 38° C. while being irradiated and cooled, without inert gas blanketing. After only about 3 minutes, the perfluorooctyl bromide becomes pink-colored due to elemental iodine being split off from the perfluoroalkyl iodides. After 15 minutes, 1 hour and 8 hours, samples are taken and the samples are separated off from the iodine by extraction by shaking with 2 M sodium hydroxide solution and distilled water and analyzed by capillary gas chromatography. A total of 396.5 g of perfluorooctyl bromide is recovered.

The perfluorooctyl bromide recovered is heated at the reflux temperature with 50 ml of 2 M sodium hydroxide solution for 2 hours, while stirring intensively, the sodium hydroxide solution is removed and the product is washed with distilled water and distilled under normal pressure. The perfluorooctyl bromide which passes over at an overhead temperature of 141° C. has a purity of more than 99.9%.

| Irradiation time | Content [% (w/w)] of: | | | | | |
| --- | --- | --- | --- | --- | --- | --- |
| | $CF_3(CF_2)_5I$ | $CF_3(CF_2)_6I$ | $CF_3(CF_2)_7I$ | $CF_3(CF_2)_5Br$ | $CF_3(CF_2)_6Br$ | $CF_3(CF_2)_7Br$ |
| 0 minute | 0.017 | 0.011 | 0.018 | <0.001 | <0.001 | 99.83 |
| 15 minutes | 0.0065 | 0.0045 | 0.0066 | <0.001 | <0.001 | 99.85 |
| 1 hour | <0.0005 | <0.0005 | 0.0006 | <0.001 | <0.001 | 99.86 |
| 8 hours | <0.0005 | <0.0005 | 0.0006 | <0.001 | <0.001 | 99.85 |

EXAMPLE 2

Example 1 is repeated, with the modification that 0.3 g of bromine is added to the perfluorooctyl bromide before the irradiation (and the treatment is carried out with sodium bicarbonate solution instead of sodium hydroxide solution). The molar ratio of bromine to the sum of perfluoroalkyl iodides is 5 : 1. The reaction temperature is 38° C. After an irradiation time of 10 minutes, 20 minutes, 30 minutes, 1 hour, 2 hours and 8 hours, samples are taken and are extracted by shaking with aqueous sodium bicarbonate solution containing 0.5 g of $NaHCO_3$ per 100 g of solution and with distilled water. The results of the analysis by capillary gas chromatography are given in the following table.

A total of 395 g of perfluorooctyl bromide is isolated.

| Irradiation | Content [% (w/w)] of: | | | | | |
|---|---|---|---|---|---|---|
| time | $CF_3(CF_2)_5I$ | $CF_3(CF_2)_6I$ | $CF_3(CF_2)_7I$ | $CF_3(CF_2)_5Br$ | $CF_3(CF_2)_6Br$ | $CF_3(CF_2)_7Br$ |
| 0 minute | 0.017 | 0.011 | 0.018 | <0.001 | <0.001 | 99.83 |
| 10 minutes | 0.0077 | 0.0052 | 0.0085 | 0.0035 | 0.0024 | 99.85 |
| 20 minutes | 0.0025 | 0.0021 | 0.0033 | 0.0058 | 0.0036 | 99.86 |
| 30 minutes | 0.0008 | 0.0011 | 0.0014 | | 0.0038 | 99.84 |
| 1 hour | <0.0005 | <0.0005 | <0.0005 | 0.0083 | 0.0043 | 99.86 |
| 2 hours | <0.0005 | <0.0005 | <0.0005 | 0.0090 | 0.0055 | 99.86 |
| 8 hours | <0.0005 | <0.0005 | <0.0005 | 0.014 | 0.0098 | 99.85 |

EXAMPLE 3

Example 1 is repeated, with the modification that the treatment with sodium hydroxide solution is omitted and that the elemental iodine formed by the irradiation is removed during the irradiation outside the irradiation apparatus by extraction by stirring with dilute aqueous sodium thiosulfate solution containing 5 g of $Na_2S_2O_3$ per 100 g of solution, and the then colorless perfluorooctyl bromide is recycled to the irradiation apparatus, after the aqueous phase has been separated off. After 10 minutes, 20 minutes, 30 minutes and 1 hour, samples are taken for capillary gas chromatography analysis.

A total of 391 g of perfluorooctyl bromide is isolated again.

| Irradiation | Content [% (w/w)] of: | | | | | |
|---|---|---|---|---|---|---|
| time | $CF_3(CF_2)_5I$ | $CF_3(CF_2)_6I$ | $CF_3(CF_2)_7I$ | $CF_3(CF_2)_5Br$ | $CF_3(CF_2)_6Br$ | $CF_3(CF_2)_7Br$ |
| 0 minute | 0.017 | 0.011 | 0.018 | <0.001 | <0.001 | 99.83 |
| 10 minutes | 0.0072 | 0.0048 | 0.0071 | <0.001 | <0.001 | 99.85 |
| 20 minutes | 0.0011 | 0.0013 | 0.0016 | 0.0015 | <0.001 | 99.86 |
| 30 minutes | <0.0005 | <0.0005 | <0.0005 | 0.0013 | <0.001 | 99.87 |
| 1 hour | <0.0005 | <0.0005 | <0.0005 | <0.001 | <0.001 | 99.86 |

EXAMPLE 4

350 g of perfluorooctyl bromide containing 0.021% (w/w) of perfluorohexyl iodide, 0.013% (w/w) of perfluoroheptyl iodide and 0.020% (w/w) of perfluorooctyl iodide are introduced into the irradiation apparatus described in Example 1, and 5 ml of isopropanol and 45 ml of 1 molar aqueous sodium hydroxide solution are added. The two-phase mixture is stirred intensively while being irradiated with a high pressure mercury lamp with an immersion tube of Duran 50 and cooled. The pH remains alkaline during the 4 hours of irradiation. After 1 hour and after 4 hours, a sample is taken from the perfluorooctyl bromide and the perfluorooctyl bromide is extracted three times with distilled water. The results of the capillary gas chromatography analysis are shown in the following table. A total of 342 g of perfluorooctyl bromide is recovered.

| Irradiation | Content [% (w/w)] of: | | | |
|---|---|---|---|---|
| time | $CF_3(CF_2)_5I$ | $CF_3(CF_2)_6I$ | $CF_3(CF_2)_7I$ | $CF_3(CF_2)_7Br$ |
| 0 minute | 0.021 | 0.013 | 0.020 | 99.81 |
| 1 hour | <0.0005 | <0.0005 | 0.0007 | 99.86 |

-continued

| Irradiation | Content [% (w/w)] of: | | | |
|---|---|---|---|---|
| time | $CF_3(CF_2)_5I$ | $CF_3(CF_2)_6I$ | $CF_3(CF_2)_7I$ | $CF_3(CF_2)_7Br$ |
| 4 hours | <0.0005 | <0.0005 | <0.0005 | 99.87 |

EXAMPLE 5

300.5 g of perfluorooctyl bromide containing 0.021% (w/w) of perfluorohexyl iodide, 0.013% (w/w) of perfluoroheptyl iodide and 0.020% (w/w) of perfluorooctyl iodide are introduced into the irradiation apparatus described in Example 1, and 100 ml of 0.1 molar aqueous sodium hydroxide solution are added. A weak stream of oxygen under a pressure of 1 bar is passed through the two-phase mixture and the mixture is stirred intensively. The perfluorooctyl bromide is irradiated with a high pressure mercury lamp with an immersion tube of Duran 50 while cooling at an internal temperature of 39° C and passing in further oxygen. After 1 hour, a sample of the perfluorooctyl bromide is taken, and after 8 hours the perfluorooctyl bromide is separated off from the upper alkaline aqueous phase, extracted by shaking with distilled water and analyzed by capillary gas chromatography. A total of 298 g of perfluorooctyl bromide is recovered.

After the irradiation, the alkaline aqueous phase contains traces of the sodium salts of perfluoroalkanecarboxylic acids which have formed from the perfluoroalkyl iodides.

| Irradiation | Content [% (w/w)] of: | | | | | |
|---|---|---|---|---|---|---|
| time | $CF_3(CF_2)_5I$ | $CF_3(CF_2)_6I$ | $CF_3(CF_2)_7I$ | $CF_3(CF_2)_5CF_3$ | $CF_3(CF_2)_6CF_3$ | $CF_3(CF_2)_7Br$ |
| 0 minute | 0.021 | 0.013 | 0.020 | <0.001 | <0.001 | 99.81 |
| 1 hour | <0.0005 | <0.0005 | <0.0005 | 0.0015 | <0.001 | 99.87 |
| 8 hours | <0.0005 | <0.0005 | <0.0005 | <0.001 | <0.001 | 99.86 |

EXAMPLE 6

300.5 g of perfluorooctyl bromide containing 0.021% (w/w) of perfluorohexyl iodide, 0.013% (w/w) of perfluoroheptyl iodide and 0.020% (w/w) of perfluorooctyl iodide are introduced into the irradiation apparatus described in Example 1, and 100 ml of 0.1 molar aqueous sodium hydroxide solution are added. The perfluorooctyl bromide and the sodium hydroxide solution are freed from dissolved atmospheric oxygen by several operations of partial evacuation of the gas phase and introduction of nitrogen into the two liquid phases, while stirring. The perfluorooctyl bromide is irradiated with a high pressure mercury lamp with an immersion tube of Duran 50 while cooling at an internal temperature of 35° C. and while passing in a further weak stream of nitrogen and stirring. After 1 hour, a sample is taken from the perfluorooctyl bromide, and after 8 hours the perfluorooctyl bromide is separated off from the upper alkaline aqueous phase, extracted by shaking with distilled water and analyzed by capillary gas chromatography. A total of 297 g of perfluorooctyl bromide is recovered.

In the absence of oxygen, the perfluoroalkyl radicals $R_F$ formed photochemically dimerize to give perfluoroalkanes $R_F$-$R_F$, which can be separated off from the perfluoroalkyl bromides of the formula $R_F$Br by distillation.

| Irradiation time | Content [% (w/w)] of: | | | | | |
|---|---|---|---|---|---|---|
| | $CF_3(CF_2)_5I$ | $CF_3(CF_2)_6I$ | $CF_3(CF_2)_7I$ | $CF_3(CF_2)_{12}CF_3$ | $CF_3(CF_2)_{14}CF_3$ | $CF_3(CF_2)_7Br$ |
| 0 minute | 0.021 | 0.013 | 0.020 | <0.001 | <0.001 | 99.81 |
| 1 hour | 0.013 | 0.0093 | 0.020 | 0.0012 | <0.001 | 99.83 |
| 8 hours | <0.0005 | <0.0005 | 0.011 | 0.0070 | 0.016 | 99.83 |

EXAMPLE 7

400 g of perfluorooctyl bromide and 0.3 g of bromine are introduced into a cylindrical irradiation apparatus (internal diameter: 5.5 cm, height: 20 cm) with jacket cooling, a Heraeus laboratory immersion lamp comprising the TNN 15/32 low pressure mercury vapor lamp and an immersion tube of quartz (virtually monochromatic radiation flux at 254 nm: about 6 watt), an intensive cooler with a CaCl$_2$ drying tube, an internal thermometer and a magnetic stirring fish. According to capillary gas chromatography determination, the perfluorooctyl bromide contains 0.017% (w/w) of perfluorohexyl iodide, 0.011% (w/w) of perfluoroheptyl iodide and 0.018% (w/w) of perfluorooctyl iodide. The molar ratio of bromine to the sum of the perfluoroalkyl iodides is 5 : 1. The solution is stirred at 30 to 35° C under UV irradiation. After an irradiation time of 1 hour and 8 hours, samples are taken for capillary gas chromatography analysis, and after 8 hours the entire batch is extracted twice by shaking with 2 M sodium hydroxide solution and with distilled water. A total of 391 g of perfluorooctyl bromide is recovered.

It can be seen from the values in the table that short-wavelength UV light of wavelength 254 nm breaks down the carbon chain of perfluorooctyl bromide to a small extent, whereby the purity of the perfluorooctyl bromide deteriorates.

| Irradiation time | Content [% (w/w)] of: | | | | | |
|---|---|---|---|---|---|---|
| | $CF_3(CF_2)_5I$ | $CF_3(CF_2)_6I$ | $CF_3(CF_2)_7I$ | $CF_3(CF_2)_5Br$ | $CF_3(CF_2)_6Br$ | $CF_3(CF_2)_7Br$ |
| 0 minute | 0.017 | 0.011 | 0.018 | <0.001 | <0.001 | 99.83 |
| 1 hour | 0.0097 | 0.0070 | 0.013 | 0.030 | 0.059 | 99.71 |
| 8 hours | 0.0065 | <0.001 | 0.0079 | 0.085 | 0.24 | 99.43 |

EXAMPLE 8

Example 7 is repeated, with the modification that the irradiation is carried out at 18° C. without addition of 0.3 g of bromine. During the irradiation with UV light of wavelength 254 nm, traces of elemental bromine are split off from the perfluorooctyl bromide and the perfluorooctyl bromide becomes pale brown in color. After an irradiation time of 8 hours and treatment with sodium hydroxide solution as described in Example 7, 396 g of perfluorooctyl bromide ar recovered.

| Irradiation time | Content [% (w/w)] of: | | | | | |
|---|---|---|---|---|---|---|
| | $CF_3(CF_2)_5I$ | $CF_3(CF_2)_6I$ | $CF_3(CF_2)_7I$ | $CF_3(CF_2)_5Br$ | $CF_3(CF_2)_6Br$ | $CF_3(CF_2)_7Br$ |
| 0 minute | 0.017 | 0.011 | 0.018 | <0.001 | <0.001 | 99.83 |
| 8 hours | 0.0064 | 0.0014 | 0.012 | 0.11 | 0.25 | 99.34 |

I claim:

1. A process for removing impurities from a compound or compounds of the formula $$X(CF_2)_nBr \qquad (I)$$

in which

X is F, $(CF_3)_2CF$ or Br and n is a number from 2 to 16, which comprises irradiating the mixture to be purified with electromagnetic radiation in the wavelength range from 230 to 500 nm, bringing the mixture into contact, during or after the irradiation, with at least one of the following agents: active charcoal; a finely divided solid selected from the group consisting of Cu, CuI, Ag, Mg, Zn, Al, Mn, Fe, Co, Ni and an alkali metal borohydride; chlorine, bromine, oxygen ; aqueous solutions of H$_2$O$_2$, other inorganic peroxidic compounds or alkali metal salts with the following anions: $SO_3^{2-}$, $S_2O_3^{2-}$, $PO_3^{3-}$, $NO_2^-$, $CO_3^{2-}$, $HCO_3^-$, $BrO_3^-$, $ClO_3^-$; aqueous or alcoholic solutions of alkali metal hydroxides, iodides or alcoholates or lower aliphatic alcohols, removing the agent after the treatment has ended and, optionally washing the mixture to be purified with water and distilling it.

2. The process as claimed in claim 1, wherein the mixture to be purified is liquid.

3. The process as claimed in claim 1, wherein the mixture to be purified is passed through a zone in which the irradiation takes place and then through a zone in which it comes into contact with the agent mentioned in claim 1, optionally in circulation several times in succession.

4. The process as claimed in claim 1, wherein the irradiation is carried out at a temperature which is 5° to 80° C. above the melting point of the mixture to be purified, but is not higher than 200° C.

5. The process as claimed in claim 1, wherein electromagnetic radiation is used which lies in the wavelength range from 280 to 450 nm to the extent of at least 50% of its total intensity and in which the intensity in the wavelength range below 260 nm is less than 10% of the total intensity.

6. The process as claimed in claim 1, wherein the agent with which the mixture to be purified is brought into contact is an aqueous solution of an alkali metal hydroxide, carbonate, bicarbonate or thiosulfate.

7. The process as claimed in claim 1, wherein the agent with which the mixture to be purified is brought into contact is finely divided Mg or Zn or active charcoal.

8. The process as claimed in claim 1, wherein the mixture is irradiated with electromagnetic radiation in the wavelength range from 350 to 500 nm and the agent with which the mixture to purified is brought into contact is chlorine or bromine.

9. The process as claimed in claim 1, wherein a mixture which essentially consists of at least one compound of the formula (I) in which X is F or Br and n is a number from 4 to 10 is employed.

* * * * *